United States Patent [19]

Tokura

[11] Patent Number: 5,686,994
[45] Date of Patent: Nov. 11, 1997

[54] APPEARANCE INSPECTION APPARATUS AND APPEARANCE INSPECTION METHOD OF ELECTRONIC COMPONENTS

[75] Inventor: Nobufumi Tokura, Fukuoka, Japan

[73] Assignee: Matsushita Electric Industrial Co., Ltd., Osaka, Japan

[21] Appl. No.: 703,858

[22] Filed: Aug. 27, 1996

Related U.S. Application Data

[63] Continuation of Ser. No. 264,455, Jun. 23, 1994, abandoned.

[30] Foreign Application Priority Data

Jun. 25, 1993 [JP] Japan .................................. 5-154764

[51] Int. Cl.$^6$ ................................................ G01B 11/24
[52] U.S. Cl. .................... 356/394; 356/375; 356/376; 348/126
[58] Field of Search .............................. 356/394, 237, 356/375, 376, 73, 372; 250/548, 560, 561; 348/87, 94, 125, 126; 382/154

[56] References Cited

U.S. PATENT DOCUMENTS

| | | | |
|---|---|---|---|
| 4,677,473 | 6/1987 | Okamoto et al. | 356/376 |
| 4,827,436 | 5/1989 | Sabersky et al. | 356/372 |
| 5,030,008 | 7/1991 | Scott et al. | 356/394 |
| 5,105,149 | 4/1992 | Tokura . | |
| 5,166,753 | 11/1992 | Tokura et al. | 356/394 |
| 5,272,517 | 12/1993 | Tokura | 356/375 |
| 5,293,324 | 3/1994 | Tokura | 364/552 |
| 5,406,372 | 4/1995 | Vodanovic et al. | 356/394 |

FOREIGN PATENT DOCUMENTS

| | | | |
|---|---|---|---|
| 0057837 | 3/1986 | Japan | 356/394 |
| 4203916 | 7/1992 | Japan | 356/394 |

*Primary Examiner*—Hoa Q. Pham
*Attorney, Agent, or Firm*—Ratner & Prestia

[57] ABSTRACT

A camera is part of an appearance inspection apparatus which observes electronic components soldered to a printed circuit board from a position located directly above the electronic components. The apparatus includes an illuminating light which is emitted toward the electronic components. A laser beam which is emitted from a laser oscillator to an emission area overlaps a viewing field of a camera. The camera is for acquiring image data of the electronic component. Also included is a photo sensor which is disposed obliquely above the emission area which receives the reflected light of the laser beam which has been reflected by the solder. Also included is a moving apparatus for moving the printed circuit board in a horizontal direction relative to the camera and laser oscillator. The image data is acquired and the solder height is measured at substantially the same time. As a result, inspection time is shortened.

15 Claims, 7 Drawing Sheets

FIG. 9
PRIOR ART

APPEARANCE INSPECTION APPARATUS AND APPEARANCE INSPECTION METHOD OF ELECTRONIC COMPONENTS

This application is a continuation of application Ser. No. 08/264,455 filed Jun. 23, 1994 now abandoned.

FIELD OF THE INVENTION

The present invention relates to an appearance inspection apparatus and an appearance inspection method of electronic components for inspecting the presence or absence of mounting errors of electronic components mounted on a printed circuit board and an inspection qualification of the solder used for adhering electrodes of the electronic components to lands of a printed circuit board.

BACKGROUND OF THE INVENTION

Electronic components such as integrated circuits (IC), large scale integrated circuits (LSI), chip capacitors, and chip resistors are subjected to an appearance inspection after being soldered on a printed circuit board. An appearance inspection is roughly classified into (1) the inspection of the presence or absence of mounting errors of electronic components, and (2) an inspection qualification of the solder for adhering electrodes of electronic components to lands (electrodes) of a printed circuit board.

An inspection includes inspecting for mounting errors to determine the presence or absence of electronic components, position deviation of electronic components, face/back inversion of electronic components, right/left inversion of electronic components, standing of electronic components, and type of electronic components. A solder inspection includes inspecting for excessive solder, insufficient solder, and the presence or absence of solder bridges.

A widely used appearance inspection apparatus for inspecting electronic components includes height measuring instruments which use a camera and a laser oscillator for emitting a laser beam. The camera is advantageous because a large quantity of information is obtained since a large surface measurement of the object for a field of view can be obtained at one time. However, this apparatus can not obtain height information. In contrast, the height measuring instrument using the laser oscillator obtains a small quantity of information because the surface measurement of the entire object cannot be obtained at one time. However, this apparatus can measure the height at every point precisely.

Applicant previously proposed an appearance inspection apparatus of electronic components combined with a height measuring instrument using a camera and a laser oscillator (Japanese Laid-open Patent Hei. 3-48755 which is incorporated herein by reference). In this case, a camera is disposed above an XY table for mounting a printed circuit board, and a height measuring instrument is disposed next to the camera.

The appearance inspection using this conventional appearance inspection apparatus is described below with reference to FIG. 7 through FIG. 9.

Figure 7:
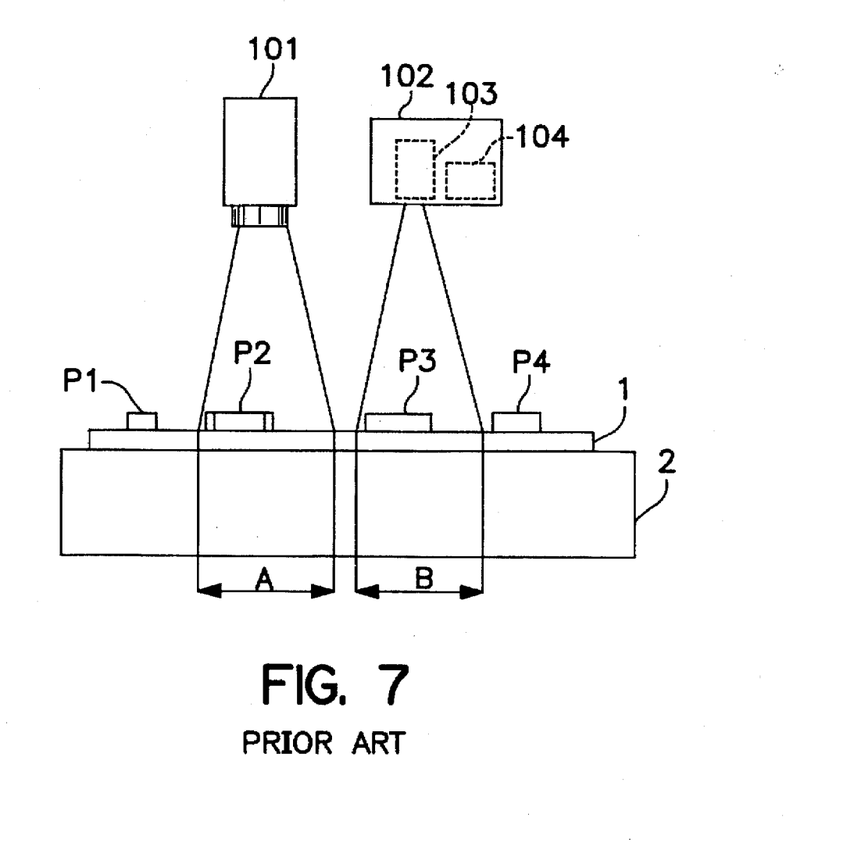
FIG. 7 is a side view of a conventional appearance inspection apparatus of electronic components.

FIG. 7 is a side view of a conventional appearance inspection apparatus for inspecting electronic components. An XY table 2 moves a printed circuit board 1 in the horizontal direction. A camera 101 is disposed above the XY table 2 and a height measuring device 102 is disposed next to the camera 101. The height measuring device 102 incorporates a laser emission part 103 for emitting a laser beam and a photo sensor 104 for receiving a reflected laser beam reflected from the surface of electronic components P1, P2, P3, P4 or solder mounted on the printed circuit board 1. A viewing field A of the camera 101 and an emission area B of laser beam from the laser emission part 103 are set at remote positions so as not to overlap each other.

Figure 8:
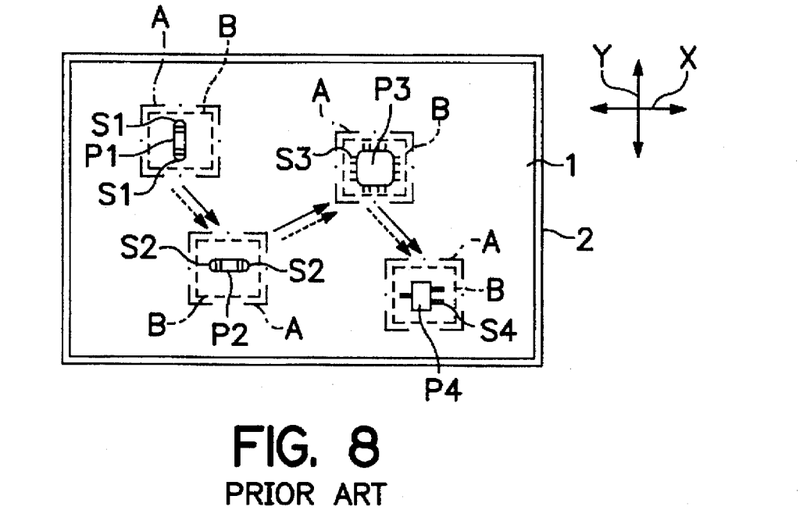
FIG. 8 is a plan view of a printed circuit board having electronic components to be inspected by the conventional appearance inspection apparatus of electronic components.

FIG. 8 is a plan view of a printed circuit board 1 mounted on the XY table 2. Multiple kinds of electronic components P1, P2, P3, P4 are mounted on the printed circuit board 1. In FIG. 8, by driving the XY table 2, the first electronic component P1 is positioned within the viewing field A of the camera. Consequently, the electronic component P1 and the solder S1 for adhering the electrode of the electronic component P1 to the land of the printed circuit board 1 are observed by the camera, acquired as image data and analyzed as image data by a computer at which time the presence or absence or deviation of the electronic component P1, or the soldering state is judged.

When inspection of the first electronic component P1 is completed, the XY table 2 is driven again, and the printed circuit board 1 is moved horizontally in the X-direction or Y-direction, and the second electronic component P2 is positioned in the camera's viewing field A. This electronic component P2 is observed by the camera, and is subjected to an appearance inspection as was the first electronic component P1. Similarly, thereafter, the third electronic component P3 and fourth electronic component P4 are appearance inspected. In FIG. 8, the solid line arrow denotes the inspection sequence by the camera. Incidentally, the number of electronic components is four in FIG. 8, but, needless to say, the number is not limited to four.

When the appearance inspection of all electronic components is completed, the solder is inspected by the height measuring device. This inspection is performed as follows. The XY table 2 is driven so that the printed circuit board 1 is moved horizontally in the X direction or Y direction to position the first electronic component P1 in the emission area B of the laser beam. A laser beam is directed towards solder S1. The reflected laser beam light is received in the photo receptor, and the height distribution of solder S1 is measured. The measured result is analyzed by a computer and the quality of the solder is judged. As mentioned above, since the height measuring device using a laser beam measures the height of the object precisely, the height measuring device is extremely good for inspecting a device to judge the quality of the solder by precisely measuring the height distribution of the solder.

When inspection of the first electronic component P1 is finished, the XY table 2 is driven again, and the printed circuit board 1 is moved horizontally in the X direction or Y direction to position the second electronic component P2 in the emission area B of the laser beam. At that time solder S2 is illuminated with the laser beam and the solder is inspected. Similarly, thereafter, the soldering state of the third electronic component P3 and fourth electronic component P4 are inspected. In FIG. 8, the broken line arrow denotes the inspection sequence by the height measuring device.

Figure 9:
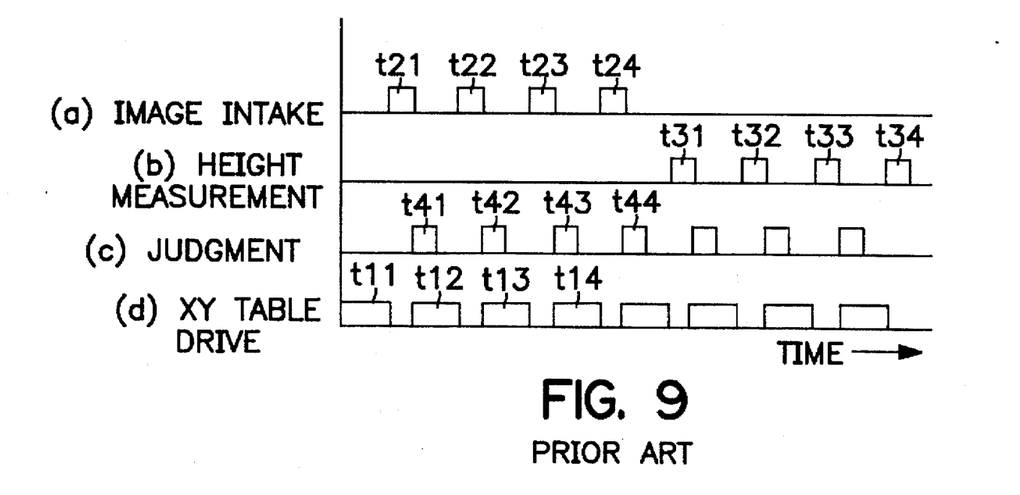
FIG. 9 is a timing chart for inspecting the appearance of electronic components by the conventional appearance inspection apparatus of electronic components.

FIG. 9 shows a time chart for conducting the appearance inspection by the appearance inspection apparatus. The chart shows the timing for the conventional appearance inspection apparatus to move the printed circuit board 1 horizontally in the X direction or Y direction by driving the XY table 2, the appearance inspection of the electronic components by the camera for, all of the electronic components P1, P2, P3, P4 and to move the XY table 2 to move the printed circuit board 1 horizontally in the X-direction or Y-direction to inspect the height of the solder for each of the electronic component.

In FIG. 9, times t11, t12, t13, t14 are driving times of the XY table 2 for moving the printed circuit board 1 horizontally, times t21, t22, t23, t24 are times for taking in images of electronic components P1, P2, P3, P4 by the camera, times t31, t32, t33, t34 are height measuring times of the solder by the height measuring device, and times t41, t42, t43, t44 are judging times by the control part of the computer. As shown in the diagram, the judging time by the computer does not affect the cycle time duration because the judgement is made in the midst of moving the printed circuit board 1 horizontally while driving XY table 2.

In such conventional appearance inspection apparatus of electronic components, however, every time an image of the electronic components P1, P2, P3, P4 is acquired or the laser beam is emitted towards solder S1, S2, S3, S4 of the electronic components P1, P2, P3, P4, the XY table 2 is driven, and the electronic components P1, P2, P3, P4 must be repositioned in the viewing field of the camera or emission area B of the laser beam. As a result, a number of driving times of the XY table 2 are required causing the appearance inspection of one printed circuit board 1 to be long. These problems are also experienced in an appearance inspection of the electronic components by the camera after a height inspection of the solder by the height measuring device is first performed.

SUMMARY OF THE INVENTION

The present invention relates to substantially shortening the time required for conducting the appearance inspection of electronic components soldered to a printed circuit board.

The appearance inspection apparatus of electronic components includes a camera for observing an electronic component adhered by solder to a printed circuit board. Also included is a light source for emitting an illuminating light toward the electronic component and a light emitter for emitting a measuring light to an emission area which overlaps the viewing field of the camera. A photo sensor is provided for receiving the reflected measuring light reflected by the solder which had been emitted from the light emitter disposed obliquely above the emission area. Also included is a moving apparatus for moving the printed circuit board and camera in the horizontal direction relatively to the light emitter.

Using the above configuration, the viewing field of the camera and the emission area of the measuring light are overlapped because the electronic component is positioned in the viewing field of the camera and the emission area of the measuring light by driving the moving apparatus. Therefore, the appearance inspection of the electronic component and solder by the camera and the inspection of the solder by the measuring light can be done without moving the printed circuit board twice. Hence, the number of times the moving apparatus moves the electronic components is reduced to half, and the time required for the appearance inspection of one printed circuit board is notably shortened.

The present invention further relates to an inspection method for inspecting electronic components which includes setting the viewing field of the camera provided above a printed circuit board and the emission area of a laser beam emitted from a laser oscillator so as to overlap each other. Then, driving a moving apparatus to move the printed circuit board horizontally relatively to the camera and laser oscillator so as to position an electronic component soldered to the printed circuit board in the viewing field and emission area Next, the method includes acquiring image data of the electronic component by the camera to be stored in a memory and measuring the solder height by a laser beam and storing the measured height data in the memory. Then, driving the moving apparatus to horizontally move the printed circuit board relatively to the camera and laser oscillator to position a next electronic component adhered by solder to the printed circuit board into the viewing field and emission area. Finally, the quality of appearance of the electronic component and solder is judge using the stored data in the memory while the moving apparatus is moving the printed circuit board.

In this method, when the electronic component is positioned within the viewing field of the camera by driving the moving apparatus in the first step, the electronic component is also positioned in the emission area of the measuring light. Subsequently, image data of the electronic component is acquired and measurement of solder height is performed simultaneously. Next, while the moving means is moving the printed circuit board, the appearance of electronic component and solder can be judged. Hence, the number of times the moving apparatus moves the printed circuit board is reduced to half, and the time required for appearance inspection of one printed circuit board can be substantially shortened.

DESCRIPTION OF THE PREFERRED EMBODIMENT

Figure 1:
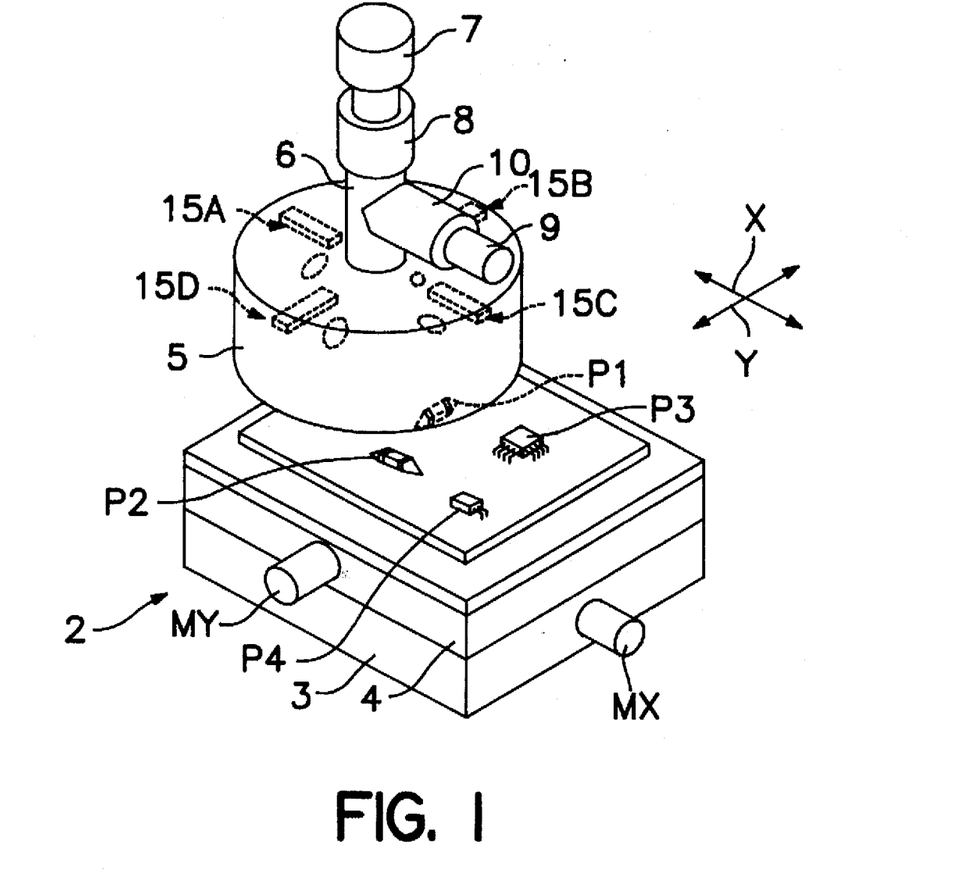
FIG. 1 is a perspective view of an appearance inspection apparatus of electronic components according to an exemplary embodiment of the present invention.
Figure 2:
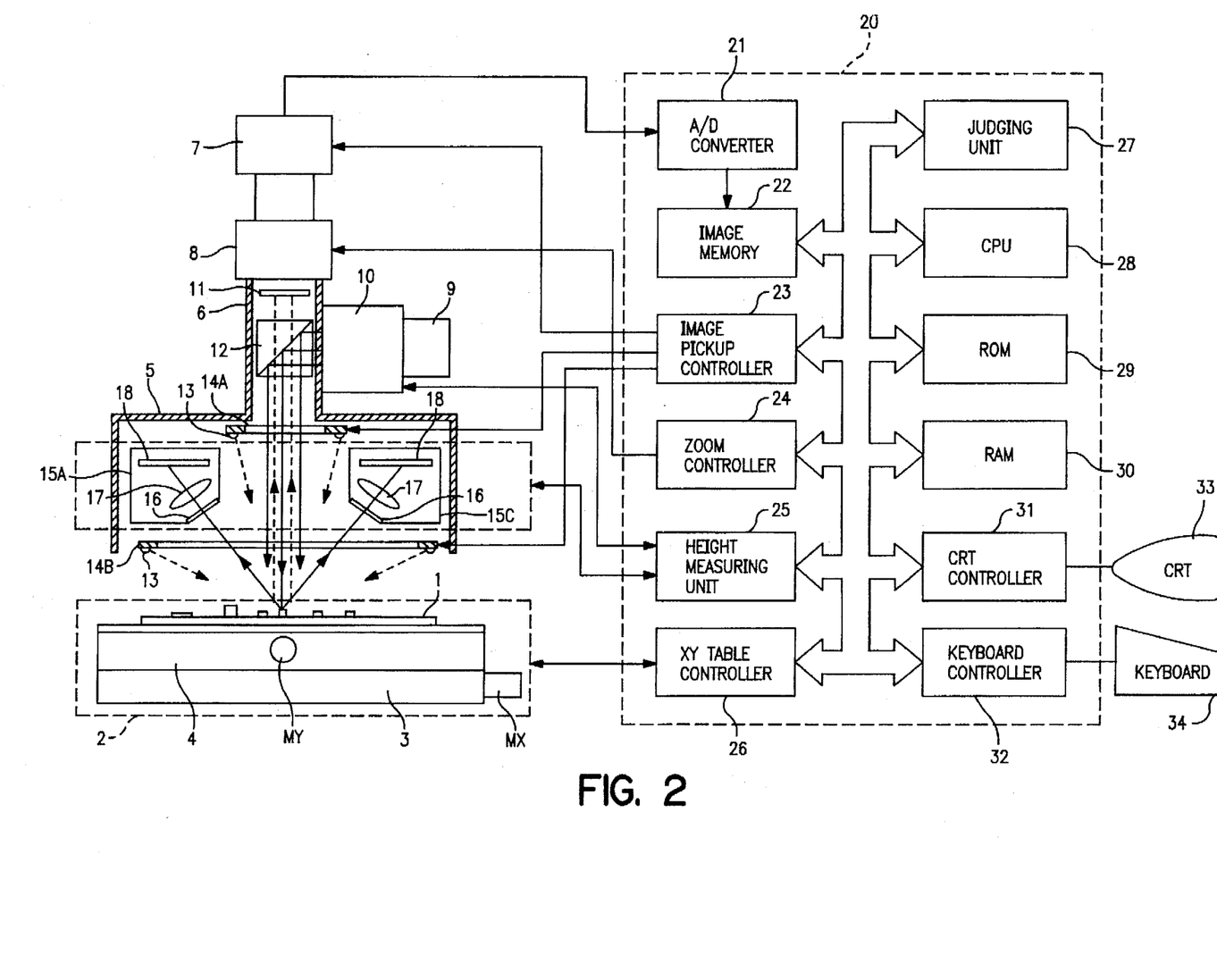
FIG. 2 is a sectional view of the appearance inspection apparatus of electronic components according to an exemplary embodiment of the present invention.

With reference to FIG. 1 and FIG. 2, an exemplary embodiment of the invention is described in detail below.

FIG. 1 is a perspective view of an appearance inspection apparatus of electronic components, and FIG. 2 is a sectional view of this appearance inspection apparatus of electronic components. As shown in the drawings, a printed circuit board 1 is placed on an XY table 2. The XY table 2 comprises an X-table 3 and a Y-table 4. When an X-direction motor MX is driven, the printed circuit board 1 moves horizontally in the X-direction, and when a Y-direction motor MY is driven, the printed circuit board 1 moves horizontally in the Y-direction.

Above the XY table 2, box 5 is disposed. A lens barrel 6 is provided above box 5. A camera 7 and a zoom mechanism 8 are provided above lens barrel 6. Camera 7 is a charge coupled device (CCD) camera. A contrast image showing bright and dark areas is acquired by a photo sensor built into camera 7. The zoom mechanism 8 adjusts the focal depth of the camera 7 so that a clear image may be acquired by the camera 7.

Next to the lens barrel 6, a laser oscillator 9 and a laser scanner 10 are provided. In the inner upper part of the lens barrel 6, a first filter 11 is provided as shown in FIG. 2, and a beam splitter 12 is disposed immediately beneath the first filter 11. A half mirror can be also used instead of the beam splitter 12. The camera 7 is disposed immediately above the printed circuit board 1, and thus, the optical path of the camera 7 is substantially perpendicular along a vertical axis to the printed circuit board 1. As a result, camera 7 observes electronic components P1, P2, P3, P4 mounted on the printed circuit board 1 from a position directly above a component. A laser beam emitted from the laser oscillator 9 is scanned in the X-direction or Y-direction by the laser scanner 10, and is reflected downward by the beam splitter 12 disposed on the optical path of the camera 7. The reflected laser beam is emitted vertically or almost vertically to the printed circuit board 1 along the optical path of the camera 7.

In FIG. 2, in the inner upper part of the box 5, an upper plate 14A and a lower plate 14B are disposed for mounting light sources 13 composed of light emitting diodes. By selectively lighting light source 13 provided on the upper plate 14A and the light source 13 provided on the lower plate 14B, the emission angle of the emitted light to the printed circuit board 1 is varied. Around the vertical optical path of the camera 7, four photo sensors 15A, 15B, 15C, 15D are radially disposed at the same circumference around the optical path (see also FIG. 1). The four photo sensors 15A, 15B, 15C, 15D have the same structure. Each photo sensor individually comprises a second filter 16, a condenser lens 17, and a detecting element 18.

The laser beam reflected by solder S enters the detecting elements 18 of the four photo sensors 15A, 15B, 15C, 15D. The detecting element 18 measures the reflection point of the laser beam, that is, the height of the measuring point, from the position of the input laser beam. The optical path of camera 7 and the optical path of the laser beam are set so that the viewing field of camera 7 and the emission area of the laser beam emitted from laser oscillator 9 may overlap each other.

Figure 3:
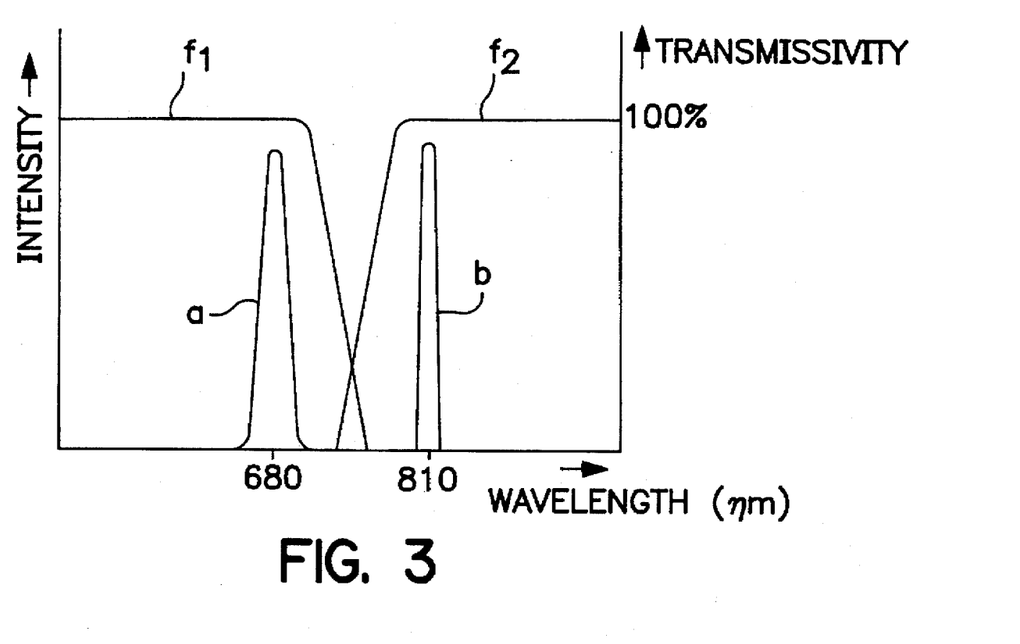
FIG. 3 is a characteristic diagram of a first filter and a second filter used in the appearance inspection apparatus of electronic components according to an exemplary embodiment of the present invention.

FIG. 3 shows the characteristics of the first filter 11 and second filter 16. In FIG. 3, curve a denotes a wavelength distribution of illuminating light by the light source 13, curve b shows a wavelength distribution of the laser beam, curve f1 shows a light transmission characteristic of the first filter 11, and curve f2 represents a light transmission characteristic of the second filter 16. The illuminating light from the light source 13 reaches its peak at a wavelength of 680 nm, while the laser beam reaches its peak at a wavelength of 810 nm. The first filter 11 has a high transmissivity of light at wavelengths of 730 nm or less, and therefore the illuminating light from the light source 13 passes through the first filter but the laser beam does not. The second filter 16 has a high transmissivity of light at a wavelength of 780 nm or more, and therefore the laser beam passes through the second filter but the illuminating light from the light source 13 does not. Hence, only the emission light from the light source 13 enters the camera 7 and not the laser beam, thereby preventing the laser beam from disturbing the image intake. In the detecting element 18, on the other hand, only the laser beam enters not the illuminating light from the light source 13, thereby preventing the illuminating light from the light source 13 from disturbing the height measurement.

In FIG. 2, a computer control unit 20 is included. Camera 7 is connected to an A/D converter 21 which converts the analog image data sent from the camera 7 to digital image data. This digital image data is stored in an image memory 22. The camera 7 is connected to an image pickup controller 23. The image pickup controller 23 controls the image intake timing of camera 7 and the lighting and extinguishing of the light source 13 according to a command from a central processing unit (cpu) 28.

The zoom mechanism 8 is connected to a zoom controller 24. The zoom controller 24 adjusts the magnification and focal depth of the camera 7 according to a command from the CPU 28. The laser scanner 10 and photo sensors 15A, 15B, 15C, 15D are connected to a height measuring unit 25. The height measuring unit 25 controls the laser scanner 10, and measures the height of the measuring point according to the incident position of the laser beam detected by the detecting element 18. The calculated height is stored in a random access memory (RAM) 30. An XY table controller 26 drives the XY table 2 and moves the printed circuit board 1 horizontally so that the desired electronic components P1, P2, P3, P4 may be positioned in the viewing field of the camera 7.

A judging unit 27 judges the presence or absence of electronic components P1, P2, P3, P4, position deviation, or soldering state, according to the image data stored in the image memory 22 and height data stored in the RAM 30. The judgement result is stored in RAM 30.

In a read-only memory (ROM) 29, program data for controlling the image pickup controller 23, zoom controller 24 and XY table controller 26 is stored. The CPU 28 controls the entire appearance inspection apparatus according to this program data. A CRT controller 31 controls a cathode-ray tube (CRT) 33 which is a display terminal. A keyboard controller 32 controls a computer keyboard 34. Each is connected by bus line 35.

Figure 4:
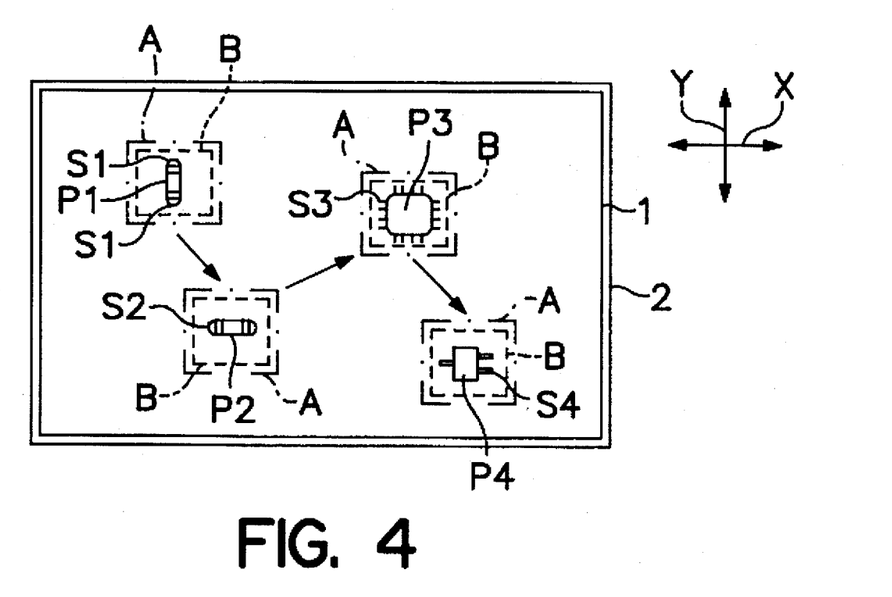
FIG. 4 is a plan view of a printed circuit board having electronic components to be inspected by the appearance inspection apparatus of electronic components.

FIG. 4 is a plan view of the printed circuit board 1 as the object of inspection being mounted on the XY table 2. Various electronic components P1, P2, P3, P4 are mounted on the printed circuit board 1. The electrodes of the electronic components P1, P2, P3, P4 are fitted to the electrodes on the printed circuit board 1 through solder S1, S2, S3, S4. The printed circuit board 1 is the same as a conventional printed circuit board 1 shown in FIG. 7. In FIG. 4, the number of electronic components is four, however, the number of components is not limited to four. In FIG. 4, viewing field A denotes the viewing field of camera 7, and emission area B shows the emission area of laser beam.

As shown in FIG. 1 and FIG. 2, since photo sensors 15A, 15B, 15C, 15D are disposed around the optical path of the camera 7, the reflected light of the laser beam emitted into the viewing field A of the camera 7 can be securely detected by photo sensors 15A, 15b, 15C, 15D. In this embodiment, one electronic component is viewed within the viewing field A and emission area B at a time, however, a plurality of electronic components can be taken in simultaneously.

Figure 5:
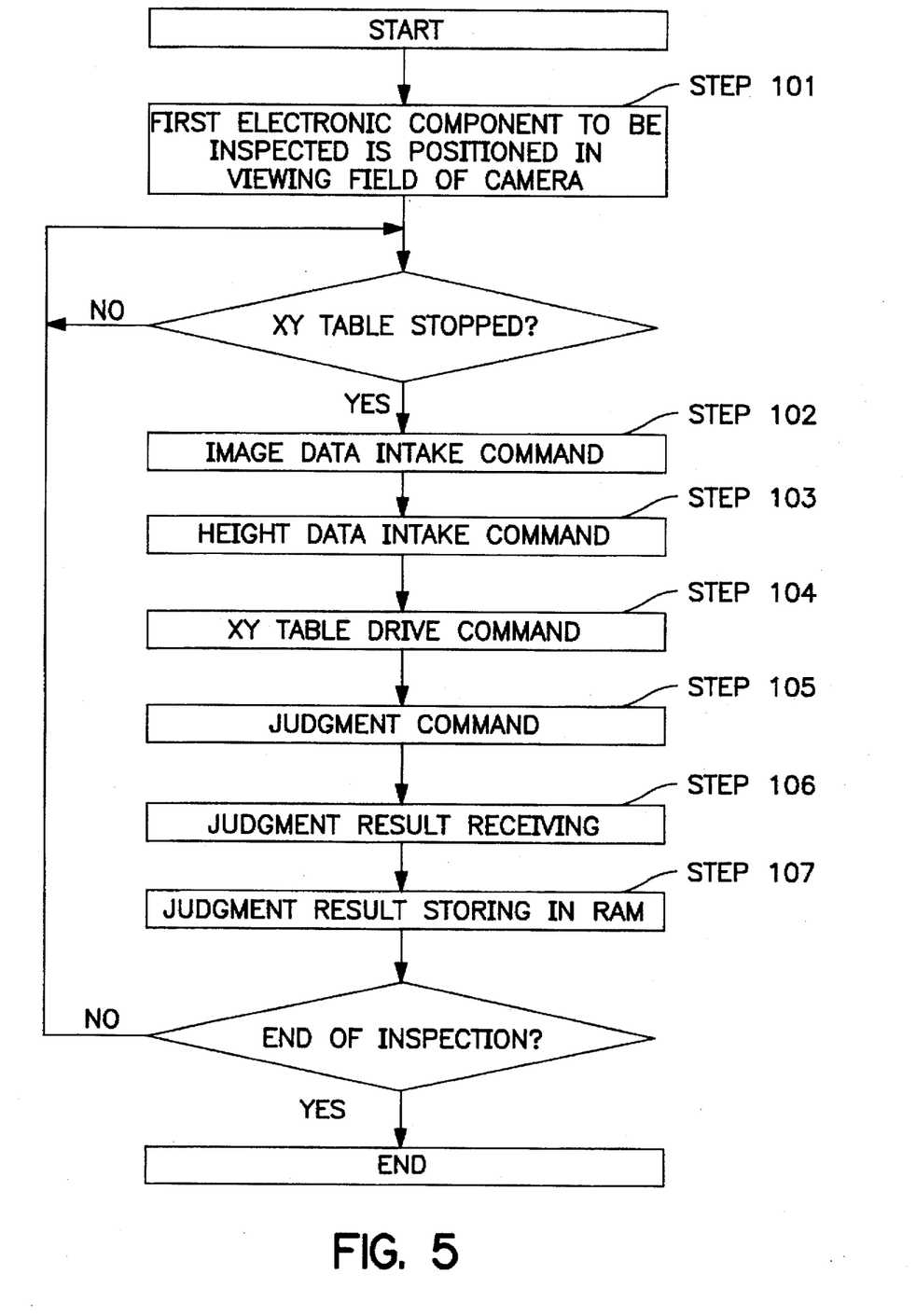
FIG. 5 is a flow chart for inspecting the appearance of electronic components by the appearance inspection apparatus of electronic components according to an exemplary embodiment of the present invention.
Figure 6:
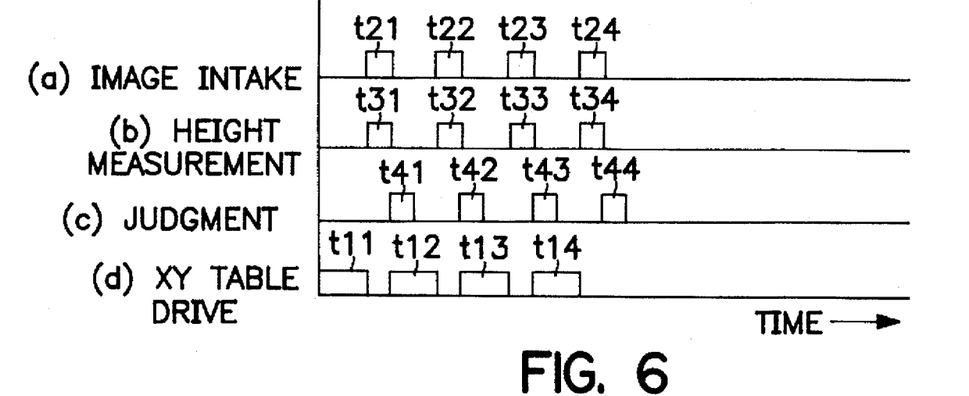
FIG. 6 is a timing chart of inspecting the appearance of electronic components by the appearance inspection apparatus of electronic components according to an exemplary embodiment of the present invention.

FIG. 5 is a flow chart of an appearance inspection, and FIG. 6 is a timing chart of the appearance inspection. In FIG. 5, at step 101, the XY table 2 is driven to move the printed circuit board 1 horizontally in the X-direction or Y-direction to position the electronic component P1 to be inspected in the viewing field A of the camera 7 at a first time.

When the XY table 2 stops, at step 102, an image intake command for camera 7 is issued from CPU 28 to the image pickup controller 23. The image data of the electronic component P1 taken into the camera 7 is converted into digital data by the A/D converter 21, and stored in the image memory 22. At the same time, at step 103, a height data intake command to laser oscillator 9 and detecting element 18 is issued from the CPU 28 to the height measuring unit 25. As a result, a laser beam is emitted from the laser oscillator 9 to obtain height distribution data of solder S1. The obtained height distribution data is stored in RAM 30. In this case, as shown in FIG. 4, since the viewing field A of the camera 7 and emission area B of the laser beam overlap, the image data of the electronic component P1 is taken in by the camera 7, and the height distribution of solder S1 of electronic component P1 is measured by the laser beam without moving the XY table 2 again.

Then when the CPU 28 recognizes the termination of data intake of the first electronic component P1, at step 104, a drive command for the XY table 2 is issued from the CPU 28 to the XY table controller 26. While the printed circuit board 1 is moving horizontally by driving XY table 2, at step 105, a judgement command as to the appearance and soldering state of the electronic component P1 is issued to the judging unit 27. Then at step 106, the CPU 28 receives the result of the judgement. This judgement result is stored in RAM 30 at step 107. When the operation is terminated, the XY table 2 stops and returns to step 102. Each step above is repeated for electronic components P2, P3, P4.

An appearance inspection method of electronic components using camera 7, for example, is disclosed in Japanese Laid-open Patent Hei. 4-1512 which is herein incorporated by reference. As the method of inspection of soldering state by laser beam, for example, a method is disclosed in Japanese Laid-open Patent Hei. 3-183906 which is incorporated herein by reference. These or other known inspection methods may be directly employed in this appearance inspection apparatus of electronic components.

FIG. 6 is a timing chart of the appearance inspection method of electronic components according to the exemplary embodiment of the present invention. In FIG. 6, t11, t12, t13, t14 are driving times of the XY table 2 for moving the printed circuit board 1 horizontally, times t21, t22, t23, t24 are times for acquiring images of electronic components P1, P2, P3, P4 by the camera, times t31, t32, t33, t34 are solder height measuring times of the solder by the laser oscillator, and times t41, t42, t43, t44 are judging times by the control unit of the computer.

In the invention, as shown in FIG. 4, since the viewing field A of the camera 7 and emission area B of laser beam are overlapped, while stopping the printed circuit board 1 in one position, the image data of the electronic component P1 can be taken in by camera 7, and the height distribution of the solder S1 of the electronic component P1 can be measured by the laser beam. That is, the image intake times t21, t22, t23, t24 and the height measuring times t31, t32, t33, t34 occur at substantially the same time. Therefore, as compared with the conventional method shown in FIG. 8, the amount of time for moving the printed circuit board 1 by driving the XY table 2 is reduced to half, and the time required for inspection of one printed circuit board 1 is notably curtailed.

In this embodiment the laser beam is intended to measure the solder height, however, by measuring the height of the electronic component by laser beam, the presence or absence of electronic component or position deviation can be inspected using the measurement. Furthermore, the printed circuit board 1 may be fixed and the optical system comprising the camera 7 and laser oscillator 9 may be moved horizontally in the X-direction or Y-direction by a moving apparatus.

According to the invention, as described herein, since the viewing field of the camera and emission area of the measuring light (laser beam) coincide, by driving the XY table to only one position, an electronic component is placed in the viewing field of the camera and in the emission area of the measuring light. As a result, an appearance inspection of the electronic components and solder by the camera, and an inspection of solder by measuring light can be conducted while the printed circuit board is stopped once. Accordingly, the XY table is not required to be moved twice to position the printed circuit board horizontally for measurements. Therefore, as compared with the conventional method, the number of times the XY table is moved is reduced to half, and the time required for appearance inspection of one printed circuit board is substantially shortened.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. An appearance inspection apparatus for inspecting a component adhered by solder to a printed circuit board, said appearance inspection apparatus comprising:

a camera for observing said component on said printed circuit board from a first position located above said component, said camera having a viewing field and said component being located in said viewing field, a light source for emitting an illuminating light toward the component, said illuminating light used by said camera for observing said component, a light emitter for emitting a measuring light from a second position located above said component to an emission area on said printed circuit board so that said emission area and said viewing field of said camera overlap, said measuring light reflecting from the solder to emit a reflected measuring light, photo sensing means for receiving the reflected measuring light, control means for maintaining said printed circuit board, said camera and said light emitter stationary until both the camera observes said component and the photo sensing means receives said reflected measuring light, and moving means for moving one of (1) the printed circuit board and (2) said camera and said light emitter in a horizontal direction after the camera observes said component and the photo sensing means receives said reflected measuring light.

2. The appearance inspection apparatus of claim 1, wherein the light emitter is a laser oscillator.

3. The appearance inspection apparatus of claim 1, wherein:

the camera has a first optical path between said camera and said component, said photo sensing means has a second optical path between said photo sensing means and said component, and the wavelength of the illuminating light and the wavelength of the measuring light are different, and the appearance inspection apparatus further includes:
- a first filter for preventing the measuring light from entering the camera, said first filter disposed in said first optical path, and
- a second filter for preventing the illuminating light from entering the photo sensing means said second filter disposed in said second optical path.

4. The appearance inspection apparatus of claim 1, wherein said first position and said second position are along the same vertical axis.

5. The appearance inspection apparatus of claim 1, wherein the camera observes said component and said photo sensing means receives said reflected light at substantially the same time.

6. The appearance inspection apparatus of claim 1, wherein said photo sensing means comprises a plurality of photo sensors radially positioned around the axis of the measuring light emitted to the emission area on the substrate.

7. The appearance inspection apparatus of claim 1, further comprising:
- memory means for storing image data obtained by the camera,
- height measuring means for calculating the height of a measuring point using a signal from the photo sensing means, and
- judging means for judging a quality of a positioning and a soldering of the electronic component on the substrate using said image data and said calculated height of the measuring point.

8. An appearance inspection method for inspecting components soldered to a printed circuit board, said appearance inspection method comprising:
- (a) setting a viewing field of a camera provided above the printed circuit board and an emission area of a laser beam emitted from a laser oscillator to overlap each other,
- (b) moving the printed circuit board horizontally relative to said camera and said laser oscillator to position a first component soldered to the printed circuit board in the viewing field and the emission area,
- (c) acquiring image data of the first component using the camera and storing said image data in a memory,
- (d) measuring a height of a measuring point using the laser beam and storing the measured height in the memory,
- (e) maintaining said printed circuit board stationary until both step (c) and step (d) have been performed,
- (f) moving the printed circuit board horizontally relative to said camera and said laser oscillator to position a next component soldered to the printed circuit board in said viewing field and said emission area, and
- (g) judging whether an appearance quality of said first component and the solder using the stored measured height and the stored image data from said memory while performing step (f).

9. The method of claim 8 wherein step (c) and (d) are preformed at substantially the same time.

10. An appearance inspection apparatus for inspecting an electronic component adhered by solder on a substrate comprising:
- a camera for observing said electric component, positioned above the substrate, wherein an optical axis of the camera is perpendicular to the substrate, said camera having a viewing field and said electric component being located in said viewing field,
- a light source which emits an illuminating light onto the substrate, said illuminating light used by said camera for observing said component,
- a light emitter which generates a measuring light,
- an optical device positioned between the substrate and the camera, said optical device directing the measuring light onto the substrate by reflecting the measuring light from the light emitter,
- a scanning means positioned between the light emitter and the optical device for scanning the measuring light so that the measuring light scans an emission area on the substrate which overlaps the viewing field of the camera, and
- a plurality of photo sensors radially positioned around the optical axis of the camera for receiving the measuring light by a reflection from the substrate.

11. The appearance inspection apparatus of claim 10, further comprising:
- memory means for storing image data obtained by the camera,
- height measuring means for calculating the height of a measuring point using a signal from at least one of said plurality photo sensors,
- judging means for judging a quality of a positioning and a soldering of the electronic component on the substrate using said image data and said calculated height of the measuring point.

12. The appearance inspection apparatus of claim 10 further comprising control means for maintaining said substrate stationary until the camera observes said component and at least one of said plurality of photo sensors receives said measuring light.

13. The appearance inspection apparatus of claim 10 further comprising positioning means for positioning the electric component soldered on the substrate to the region where the viewing field of the camera and the emission area of the measuring light are overlapping, said positioning means moves the substrate relative to the camera in a horizontal direction after the camera observes said component and at least one of said plurality of photo sensors receives said measuring light.

14. The appearance inspection apparatus of claim 10 wherein the optical axis intersects said optical device so that a portion of the measuring light from the light emitter is reflected along the optical axis.

15. An appearance inspection method for inspecting components soldered on a substrate comprising the steps of:
- (a) acquiring an image of the substrate at a camera having an optical axis perpendicular to the substrate,
- (b) emitting a measuring light along the optical axis of the camera to a measuring point inside of a viewfield of the camera,
- (c) receiving, at a photo sensor, the measuring light reflected by the substrate,
- (d) judging a quality of a positioning and a soldering of the electronic component to the substrate using said image data and a signal from the photo sensor,
- (e) maintaining the substrate stationary until both step (a) and step (c) have been performed, and
- (f) moving the substrate relative to the camera so that a next electronic component is positioned for inspection, wherein the viewfield of the camera and a viewfield of the measuring light overlap.

* * * * *